United States Patent
Fee et al.

(10) Patent No.: US 10,207,079 B2
(45) Date of Patent: Feb. 19, 2019

(54) DRAIN TUBE HOLDER SYSTEM

(71) Applicant: Red Oak Innovations, LLC, Moorhead, MN (US)

(72) Inventors: Louan R. Fee, Moorhead, MN (US); Patrick Fee, Moorhead, MN (US)

(73) Assignee: RED OAK INNOVATIONS, LLC, Moorhead, MN (US)

( * ) Notice: Subject to any disclaimer, the term of this patent is extended or adjusted under 35 U.S.C. 154(b) by 605 days.

(21) Appl. No.: 14/842,924

(22) Filed: Sep. 2, 2015

(65) Prior Publication Data
US 2017/0056630 A1 Mar. 2, 2017

(51) Int. Cl.
*A61M 25/02* (2006.01)
*A61F 5/449* (2006.01)
*A61M 1/00* (2006.01)
*A61F 5/44* (2006.01)

(52) U.S. Cl.
CPC .......... *A61M 25/02* (2013.01); *A61F 5/4408* (2013.01); *A61F 5/449* (2013.01); *A61M 1/008* (2013.01); *A61M 2025/026* (2013.01); *A61M 2025/0206* (2013.01); *A61M 2209/088* (2013.01)

(58) Field of Classification Search
CPC .......... A61M 25/02; A61M 2025/0206; A61M 2025/024; A61M 2025/0253; A61M 1/008; A61M 2209/088; A61M 2025/026; A61F 5/4408; A61F 5/449
See application file for complete search history.

(56) References Cited

U.S. PATENT DOCUMENTS

| 2,606,555 | A |   | 8/1952  | Solomon              |
|-----------|---|---|---------|----------------------|
| 4,057,066 | A |   | 11/1977 | Taylor               |
| 5,403,285 | A | * | 4/1995  | Roberts ........ A61M 25/02 |
|           |   |   |         | 604/179              |
| D365,928  | S |   | 1/1996  | Sauer                |
| 5,643,233 | A |   | 7/1997  | Turner               |
| 5,651,777 | A |   | 7/1997  | Walters              |
| 5,716,344 | A |   | 2/1998  | Kiel                 |
| 5,980,499 | A |   | 11/1999 | Ekey                 |
| D417,952  | S |   | 12/1999 | Dickson              |
| 6,032,289 | A |   | 3/2000  | Villapiano           |
| 6,055,668 | A | * | 5/2000  | Gros ........... A41D 13/1245 |
|           |   |   |         | 2/69                 |
| 6,065,659 | A |   | 5/2000  | Faz                  |

(Continued)

*Primary Examiner* — Lynne Anderson
(74) *Attorney, Agent, or Firm* — Hamre, Schumann, Mueller & Larson, P.C.

(57) ABSTRACT

A drain tube holder system for securely retaining drainage tubes and reservoir bulbs against the body without impeding movement of the wearer. The drain tube holder system generally includes a strap adapted to be secured around various portions of an individual's body such as the waist, thigh, or shoulder. A retainer attachment is fixedly or removably secured to the strap. The retainer attachment includes one or more pouches adapted to retain one or more tubes and bulbs therein, with a first end of the tube exiting the body of the individual before being secured within a tube retainer within the pouch. The pouch is also adapted to securely retain a bulb, such as a reservoir, adapted to retain fluids drained through the tube. Using the present invention, an individual may enjoy improved comfort while wearing a drainage tube, such as after a medical procedure.

12 Claims, 18 Drawing Sheets

(56) References Cited

U.S. PATENT DOCUMENTS

| | | | |
|---|---|---|---|
| 6,152,915 A | 11/2000 | Watson | |
| 6,270,485 B1 | 8/2001 | Ekey | |
| 6,296,164 B1 * | 10/2001 | Russo | A61F 5/449 |
| | | | 224/581 |
| 6,524,288 B1 | 2/2003 | Hadley-Fruit | |
| 6,544,232 B1 | 4/2003 | McDaniel | |
| 6,740,068 B1 | 5/2004 | Aruffo | |
| 7,066,919 B1 | 6/2006 | Sauerland | |
| 7,293,295 B2 * | 11/2007 | King | A41D 13/1245 |
| | | | 2/102 |
| 7,823,221 B2 * | 11/2010 | Green | A61F 5/4408 |
| | | | 2/114 |
| 7,854,020 B2 | 12/2010 | Ehrlickman | |
| 8,292,860 B1 | 10/2012 | Persichetti | |
| 8,845,608 B2 | 9/2014 | Krasikoff | |
| 9,089,198 B1 * | 7/2015 | Devereaux | A45F 5/022 |
| 2006/0173427 A1 | 8/2006 | Urbina | |
| 2007/0090135 A1 | 4/2007 | Benham | |
| 2008/0312615 A1 | 12/2008 | Hunter | |
| 2010/0249734 A1 | 9/2010 | Strang | |
| 2012/0091181 A1 | 4/2012 | Barnes | |
| 2013/0296814 A1 * | 11/2013 | Antholz | A61M 25/02 |
| | | | 604/319 |
| 2016/0256312 A1 * | 9/2016 | Mastracci | A61F 5/4408 |

* cited by examiner

DRAIN TUBE HOLDER SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a tube holder and more specifically it relates to a drain tube holder system for securely retaining drainage tubes and reservoir bulbs against the body without impeding movement of the wearer.

Description of the Related Art

Any discussion of the related art throughout the specification should in no way be considered as an admission that such related art is widely known or forms part of common general knowledge in the field.

Drain tubes are commonly used in the medical field for such reasons as extracting blood, pus, or any other built-up fluids from a wound or preventing accumulations of air. The drain tubes are typically placed in a patient by a surgeon and are common to many different medical procedures. The drain tubes are often a source of major discomfort and hardship for the patient as well as the clinical staff. Despite having been used in the medical field for many years, a system has not yet been introduced to comfortably and effectively retain the drainage tubes against the body of an individual.

Because of the inherent problems with the related art, there is a need for a new and improved drain tube holder system for securely retaining drainage tubes and reservoir bulbs against the body without impeding movement of the wearer.

BRIEF SUMMARY OF THE INVENTION

Provided herein is a tube holder which includes a strap adapted to be secured around various portions of an individual's body such as the waist, thigh, or shoulder. A retainer attachment is fixedly or removably secured to the strap. The retainer attachment includes one or more pouches adapted to retain one or more tubes and bulbs therein, with a first end of the tube exiting the body of the individual before being secured within a tube retainer within the pouch. The pouch is also adapted to securely retain a bulb, such as a reservoir, adapted to retain fluids drained through the tube.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
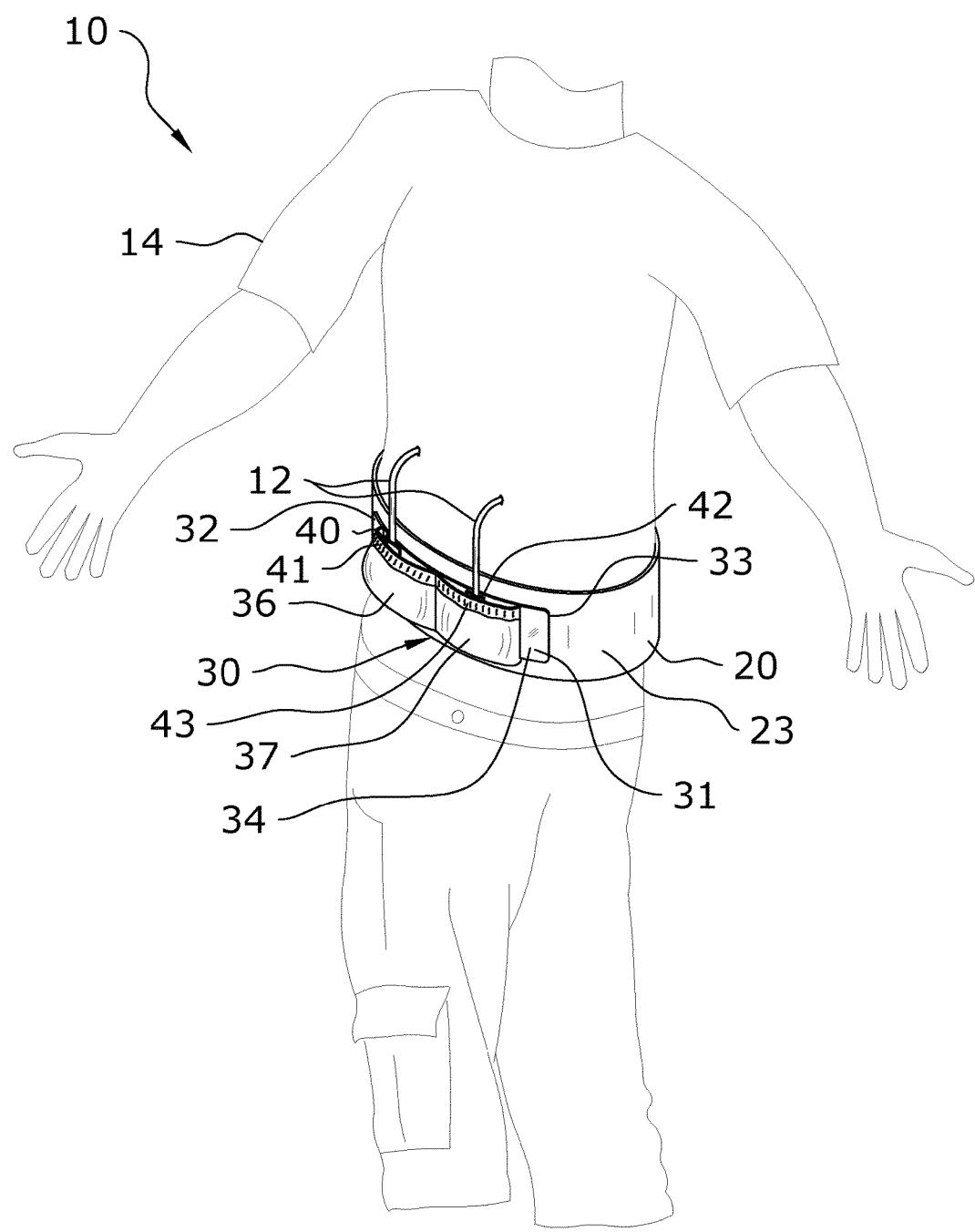
FIG. 1 is an upper perspective view of the present invention being worn around the mid-section of an individual.

Turning now descriptively to the drawings, in which similar reference characters denote similar elements throughout the several views, FIGS. 1 through 19 illustrate a drain tube holder system 10, which comprises a strap 20 adapted to be secured around various portions of an individual's 14 body such as the waist, thigh, or shoulder. A retainer attachment 30 is fixedly or removably secured to the strap 20. The retainer attachment 30 includes one or more pouches 36, 37 adapted to retain one or more tubes 12 and bulbs 13 therein, with a first end of the tube 12 exiting the body of the individual 14 before being secured within a tube retainer 40, 42 within the pouch 36, 37. The pouch 36, 37 is also adapted to securely retain a bulb 13, such as a reservoir, adapted to retain fluids drained through the tube 12.

B. Strap

Figure 9:
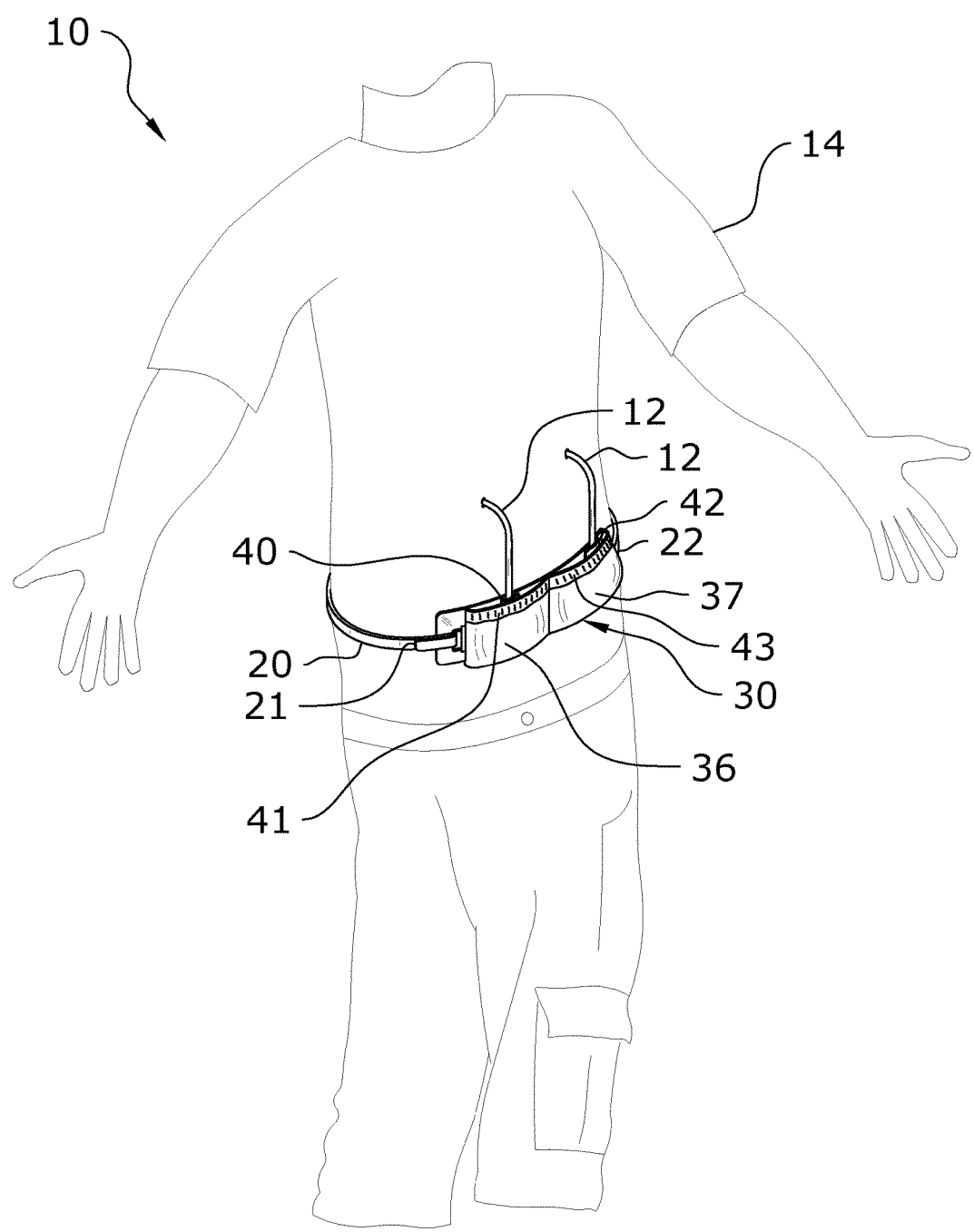
FIG. 9 is an upper perspective view of the present invention in use around the mid-section of an individual.
Figure 10:
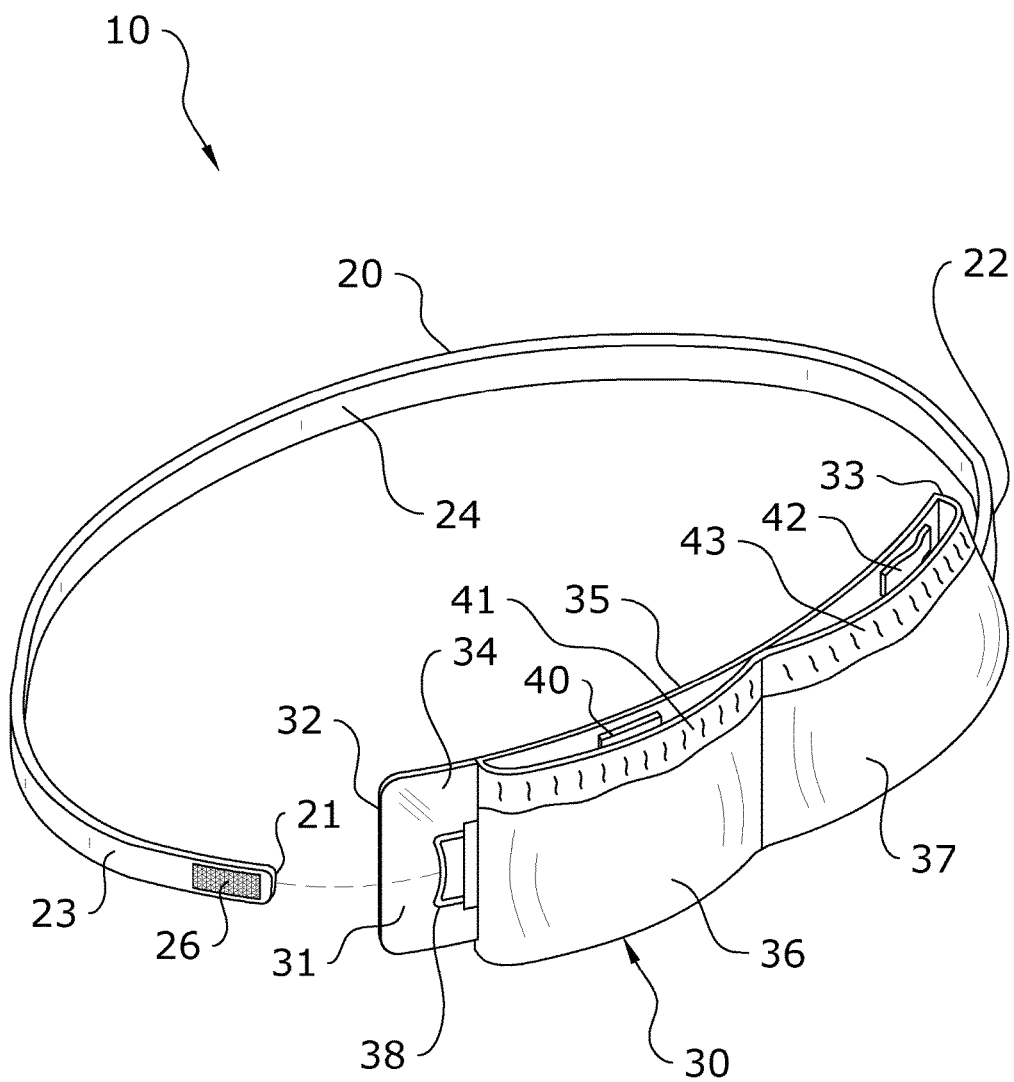
FIG. 10 is an upper perspective view of the present invention utilizing a ring structure to secure the strap to the retainer attachment.
Figure 11:
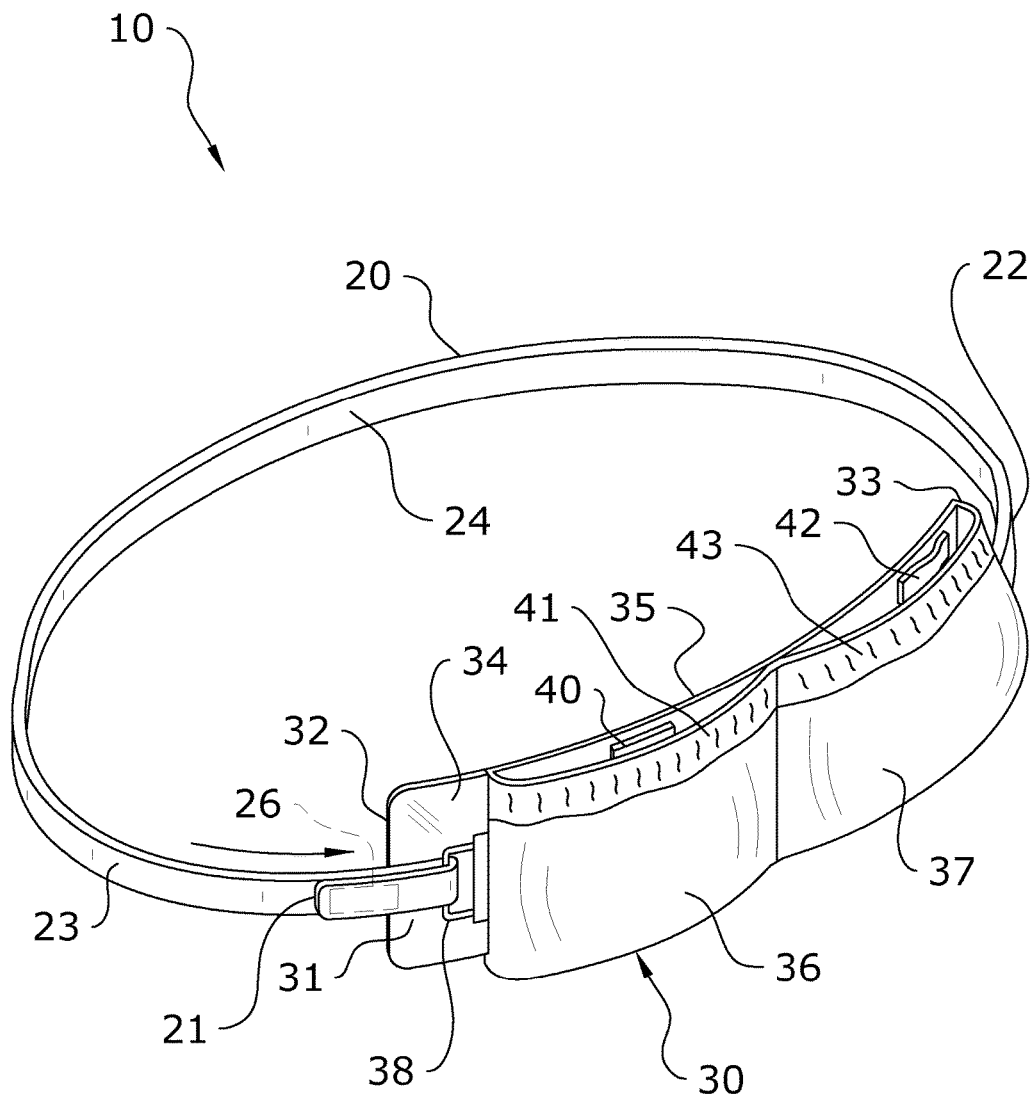
FIG. 11 is an upper perspective view of the embodiment shown in FIG. 10 in a closed position.
Figure 12:
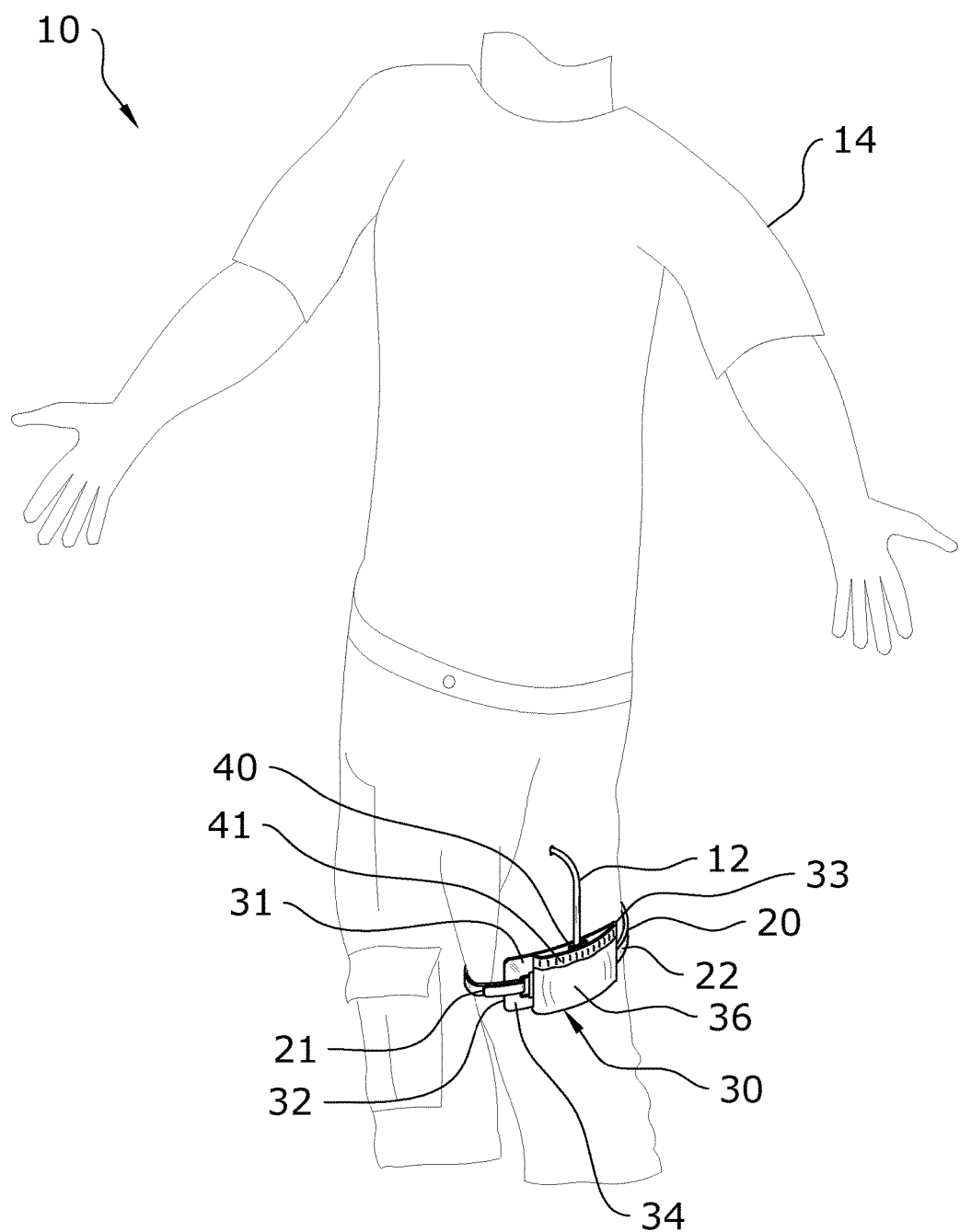
FIG. 12 is an upper perspective view of the present invention being worn around the thigh of an individual.
Figure 13:
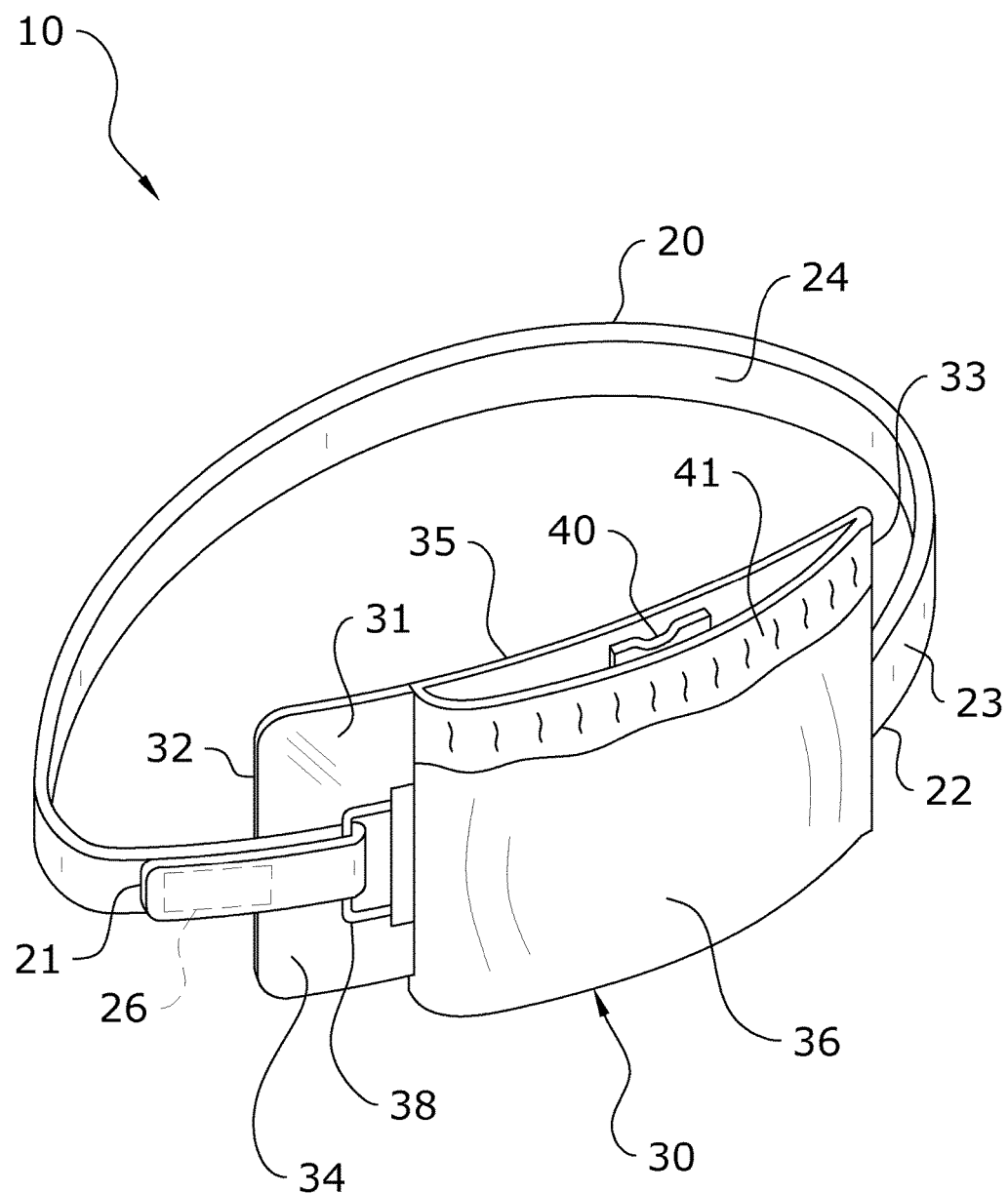
FIG. 13 is an upper perspective view of the present invention with one pouch.
Figure 14:
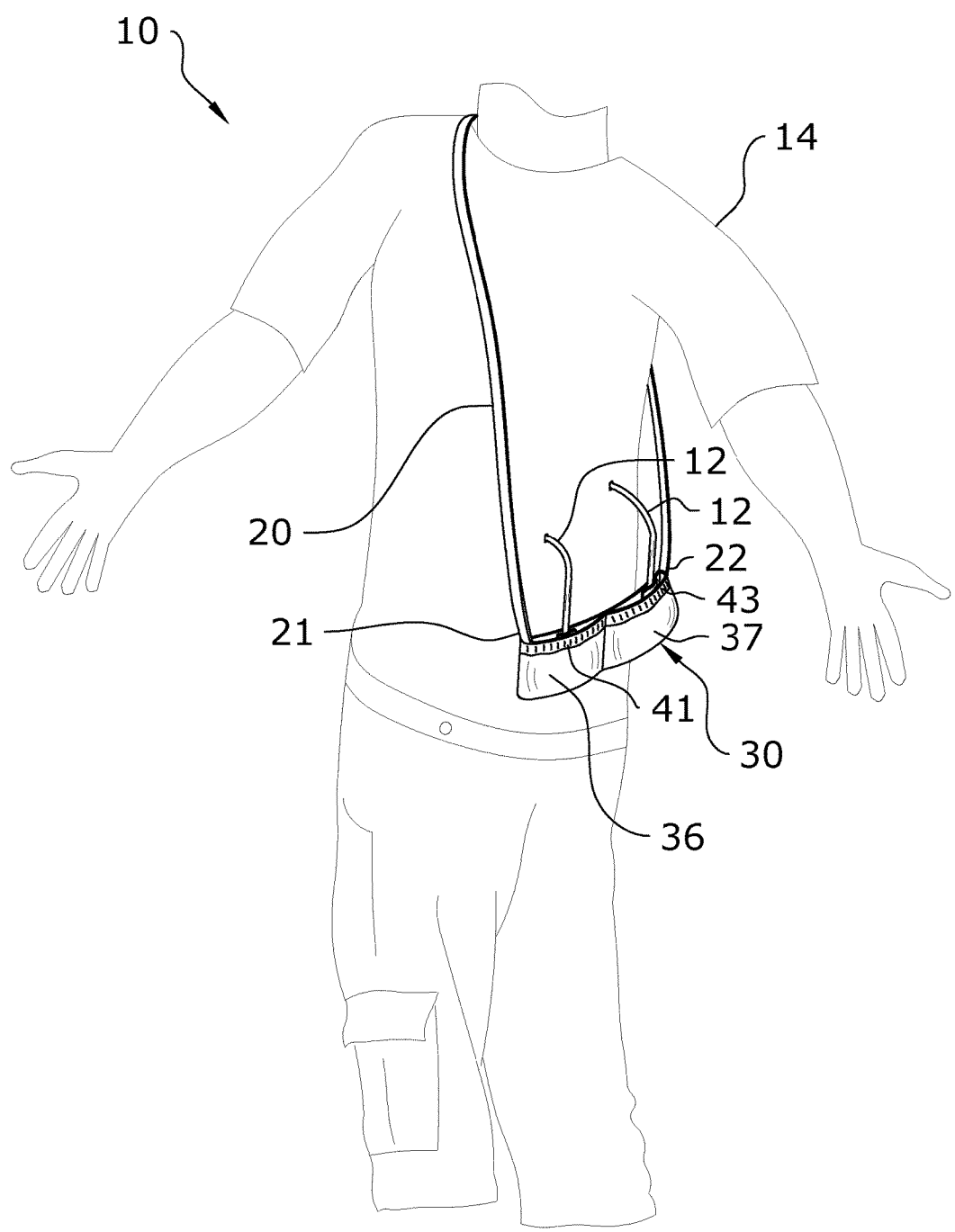
FIG. 14 is an upper perspective view of the present invention worn around the shoulder in a satchel configuration.

As shown throughout the figures, the present invention utilizes at least one strap 20 for securing the present invention to the body of an individual 14. FIGS. 1 and 9 illustrate a waist strap 20 adapted to wrap around the waist like a belt. This embodiment shows the strap 20 as comprising an abdominal compression binder with a retainer attachment. FIG. 12 illustrates the strap 20 being secured around the leg of an individual 14. FIG. 14 illustrates a shoulder strap 20 adapted to be secured around the body of the individual 14 similar to a satchel.

It should be appreciated that these are merely exemplary embodiments and thus present invention should not be construed as being limited by the exemplary figures. The present invention may be secured to the body by a wide range of methods and should not be construed as limited to any method shown in the exemplary figures.

Figure 2:
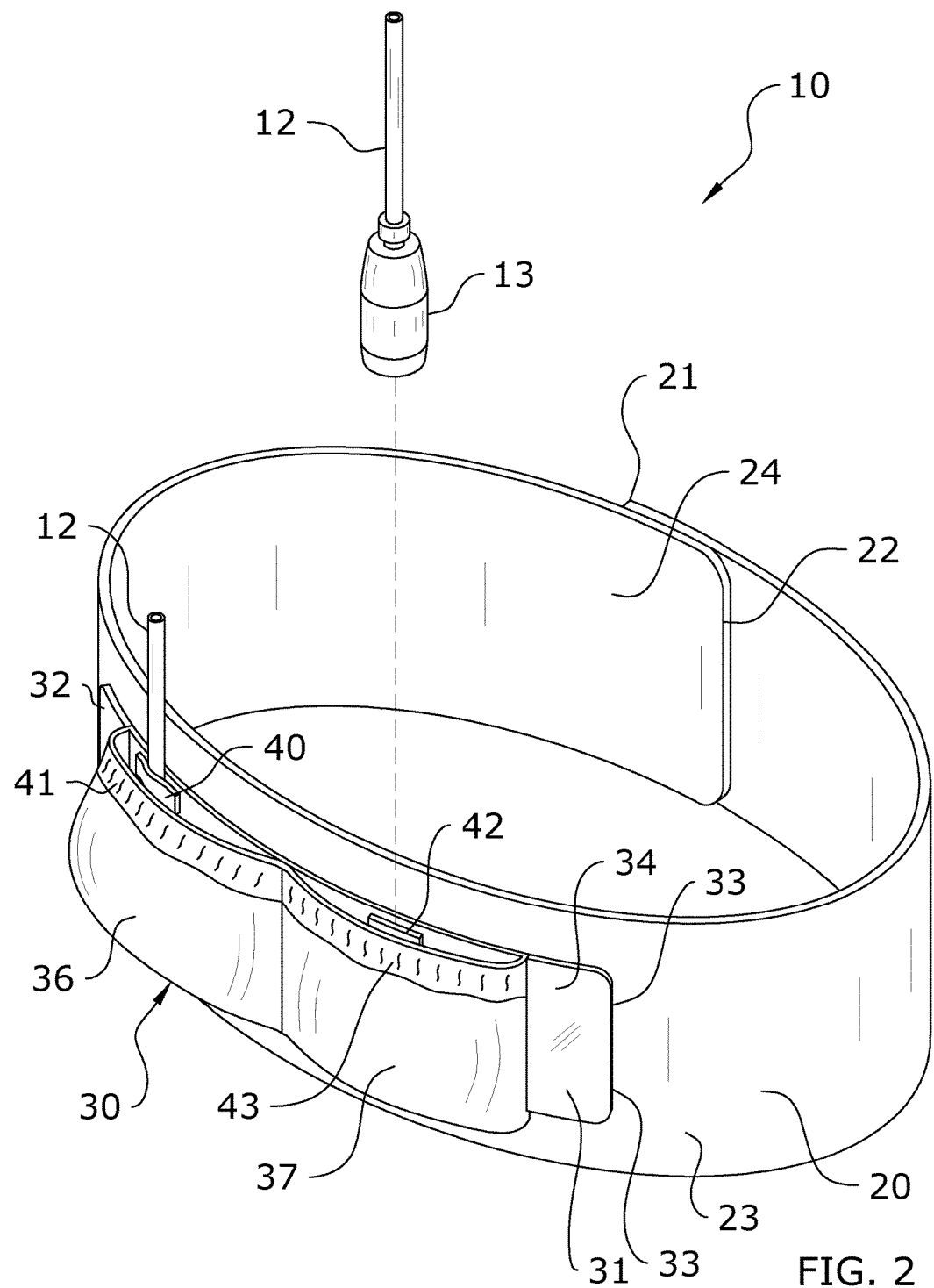
FIG. 2 is an upper perspective view of the present invention.

As shown in FIG. 2, the strap 20 generally comprises a first end 21 and a second end 22, with the first and second ends 21, 22 being adapted to secure to each other to form a continuous loop which may be placed around various portions of the body, such as the shoulder, waist, or leg as shown in the figures. The configuration, size, and orientation of the strap 20 may vary in different embodiments of the present invention. The strap 20 will preferably be sized to comfortably fit around the limb or other body portion of the individual 14 who is wearing it.

Figure 3:
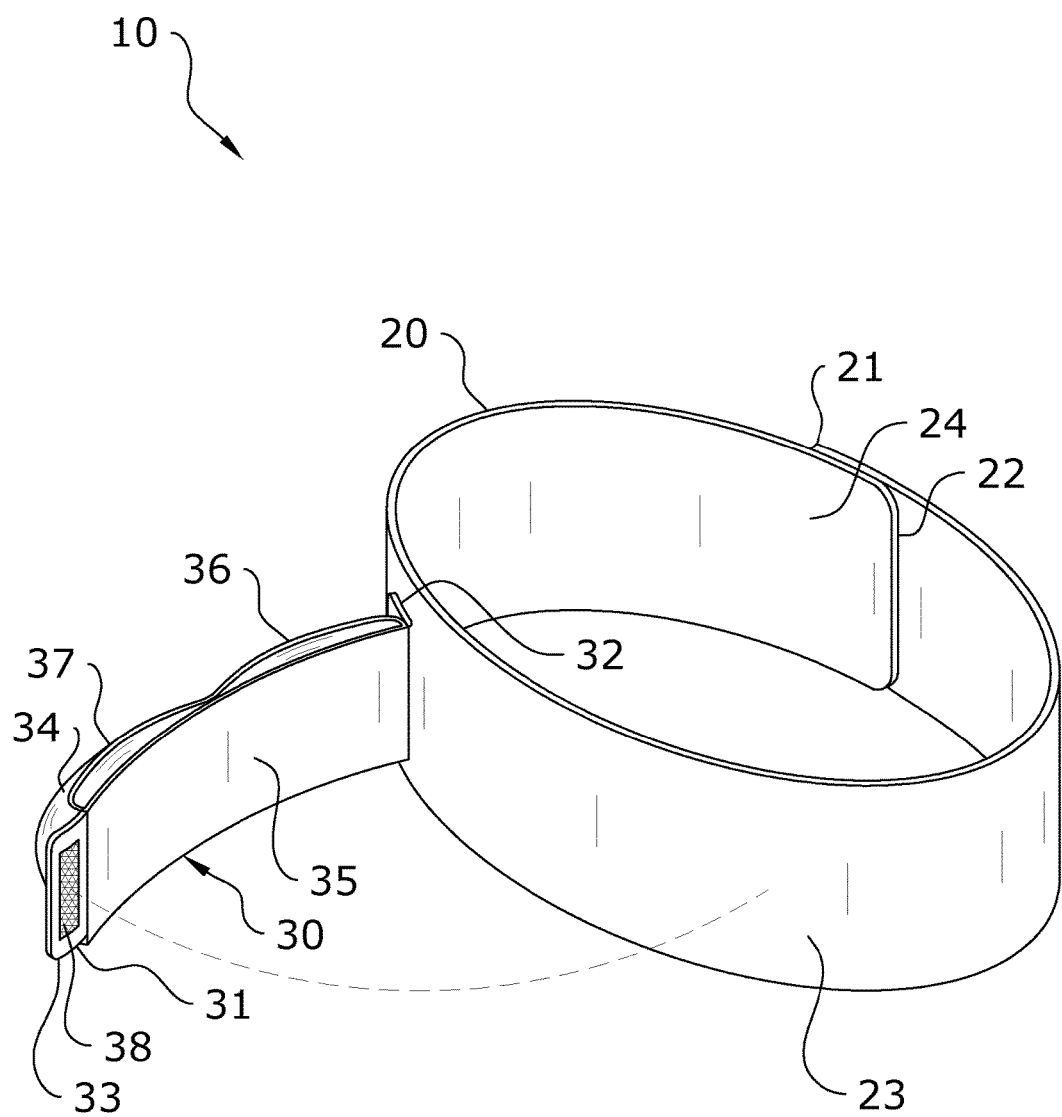
FIG. 3 is an upper perspective view of the present invention with the retainer attachment partially removed from the strap.

As shown in FIG. 2, the strap 20 includes an outer surface 23 which faces away from the body and an inner surface 24 which faces toward the body. A retainer attachment 30, described below, may be fixedly or removably attached to the outer surface 23 of the strap 20, such as shown in FIG. 3. While the strap 20 may comprise various materials and should not be limited to any particular material, the outer surface 23 of the strap 20 may comprise a material adapted to removably engage with a hook-and-loop fastener such as Velcro.

Figure 4:
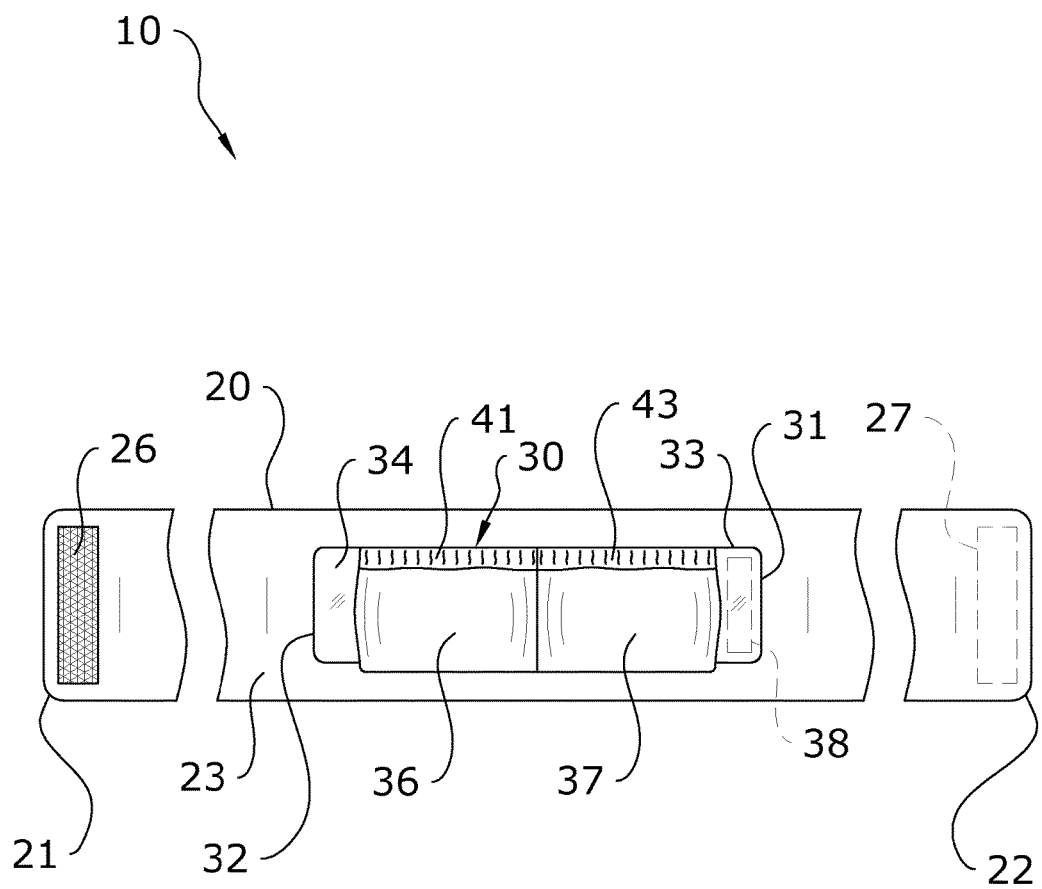
FIG. 4 is a cutaway frontal view of the present invention.
Figure 5:
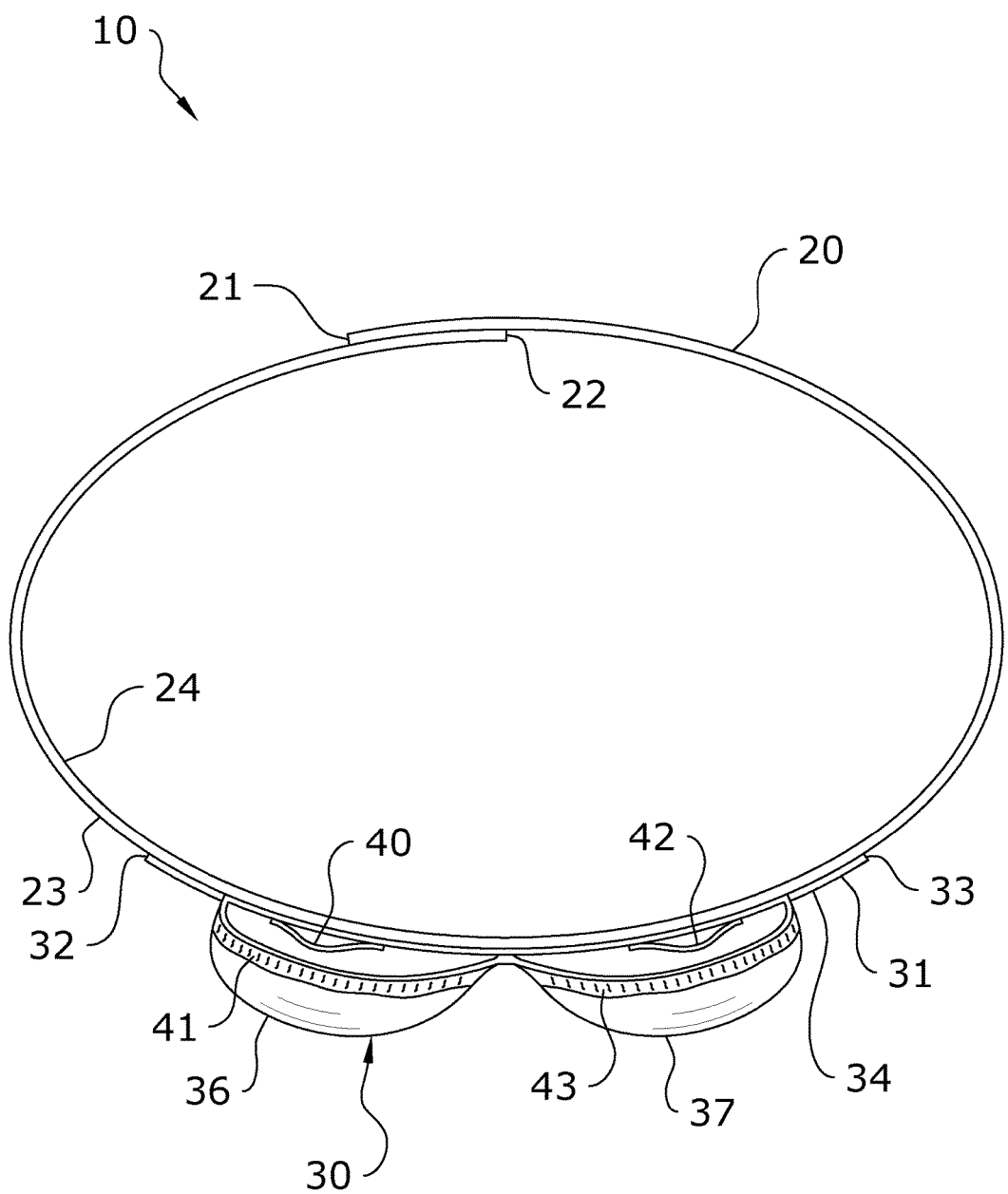
FIG. 5 is a top view of the present invention.
Figure 7:
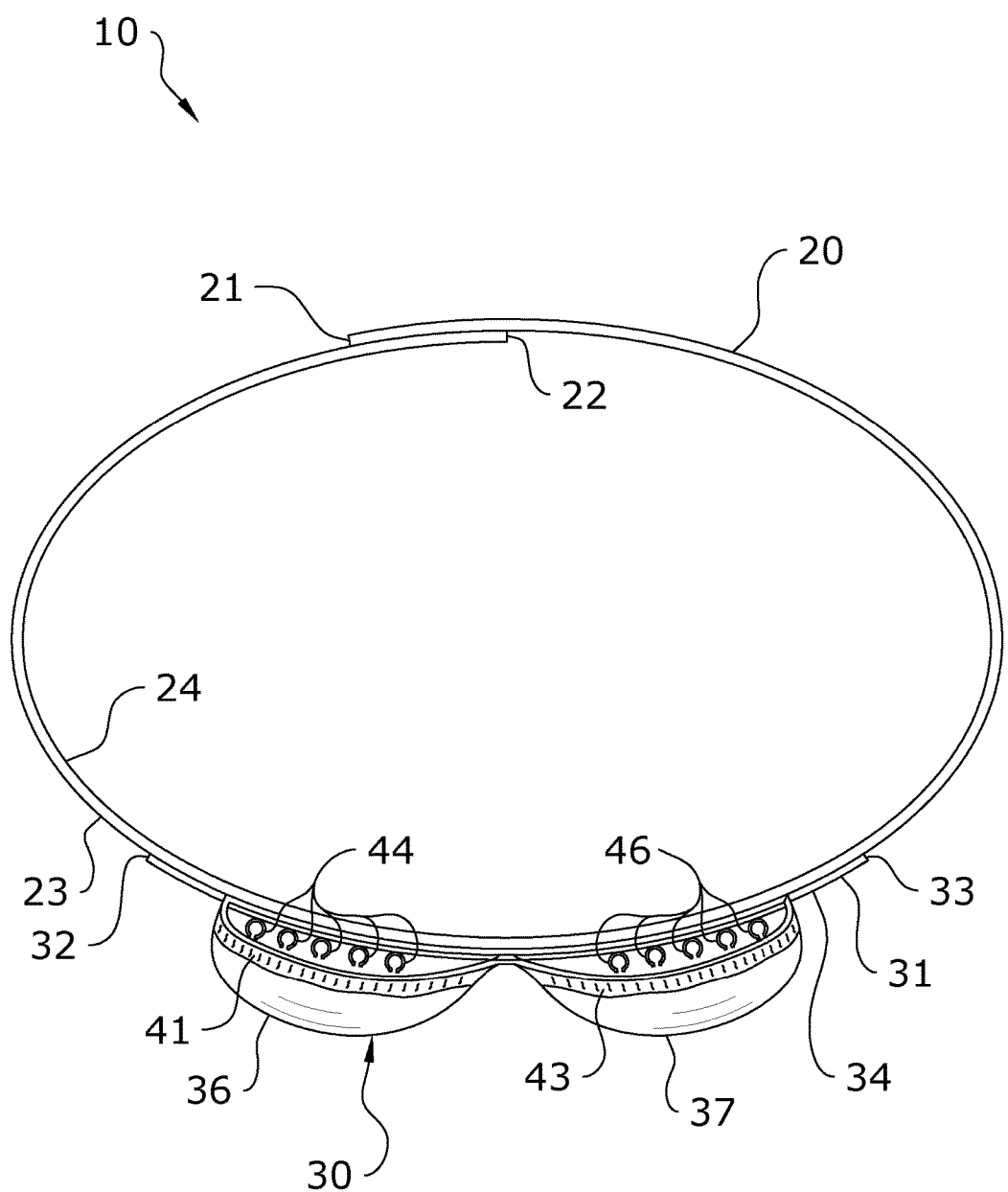
FIG. 7 is a top view of the present invention with tube retainer rows.
Figure 8:
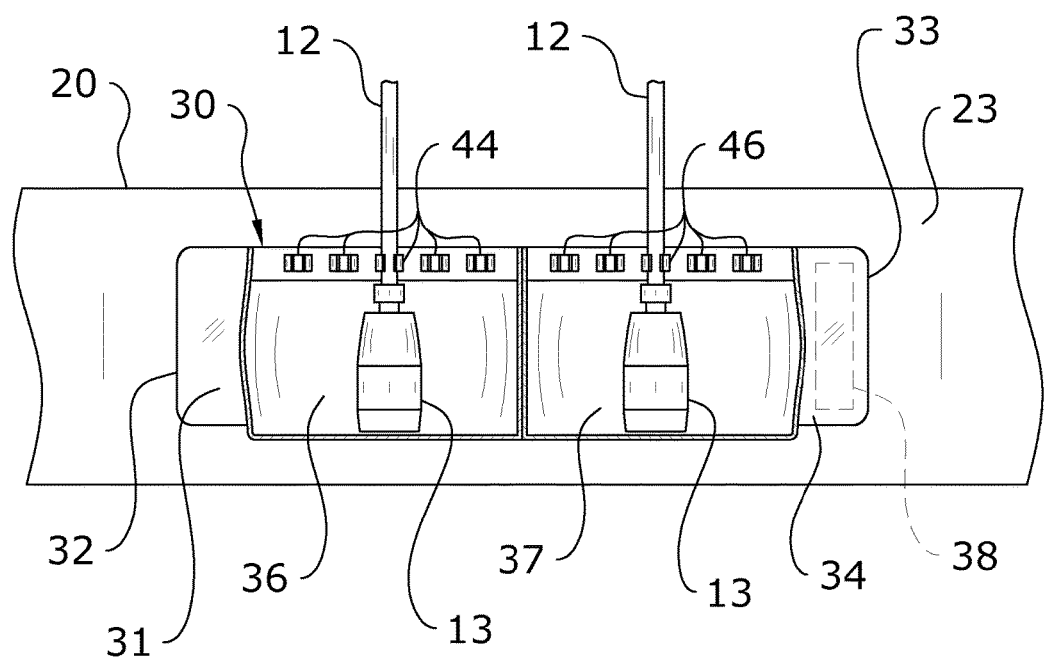
FIG. 8 is a frontal sectional view of the present invention with tube retainer rows.

The strap 20 will generally include at least one connector 26, 27 for securing the first and second ends 21, 22 of the strap 20 together to form a loop. In a preferred embodiment as shown in the figures, a first connector 26 and a second connector 27 are utilized. For example, as shown in FIG. 4, a first connector 26 may be positioned adjacent to the first end 21 of the strap 20 on its outer surface 23. A corresponding second connector 27 may be positioned adjacent to the second end 22 of the strap 20 on its inner surface 24. Thus, the first and second connectors 26, 27, illustrated as hook-and-loop fasteners but capable of being comprised of various other structures known to connect to ends 21, 22 of a strap 20 together, may be removably connected to each other as shown in FIG. 7 to form a loop of the strap 20.

Figure 15:
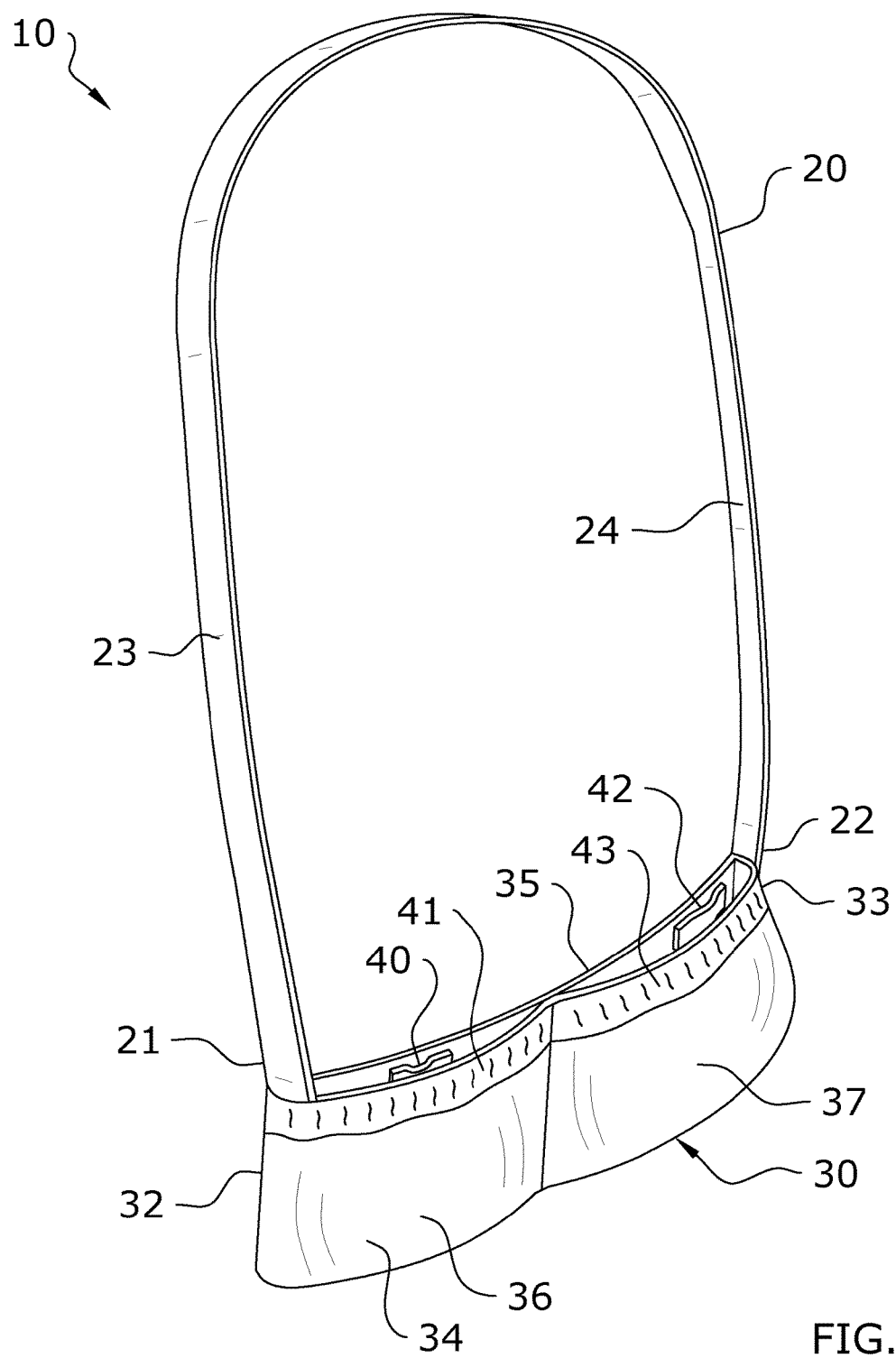
FIG. 15 is an upper perspective view of the embodiment of the present invention shown in FIG. 14.

In some embodiments, the strap 20 may not form a loop with itself but instead may form a loop in combination with the retainer attachment 30. In such an embodiment, shown in FIG. 15, the strap 20 is secured to a retainer connector 38 extending from the retainer attachment 30. In such an embodiment, the strap 20 may include a first connector 26 which connects the first end 21 of the strap 20 to the strap 20 itself as shown in FIG. 15, with the second end 22 of the strap 20 being fixedly secured to the second end 33 of the retainer attachment 30. In other embodiments, the first connector 26 may comprise a tab of double-sided Velcro material (hook-and-loop fastener) which may be inserted between two portions of the strap 20 to secure the two portions of the strap 20 together. In such embodiments, the first connector 26 may be freely removable from the strap 20. In some embodiments, the length of the strap 20 may be variable in that the strap 20 may have its length increased or decreased. For example, a standard buckle may be utilized to allow the strap 20 to be comprised of a variable length configuration. Such a configuration is preferable to allow the strap 20 to tightly but comfortably fit around a range of differently-sized bodies.

C. Retainer Attachment

As shown throughout the figures, the present invention utilizes a retainer attachment 30 which acts to secure the tube 12 and bulb 13 therein in a secure fashion. The strap 20 of the present invention allows the retainer attachment 30 to be secured at various portions of an individual's 14 body. The retainer attachment 30 may be fixedly or removably secured to the strap 20 in different embodiments of the present invention.

In a first embodiment shown in FIGS. 2, the retainer attachment 30 comprises a base 31 and a pair of pouches 36, 37 extending from the base 31. The base 31 will preferably comprise a soft material which acts as a cushion between the retainer connector 38 and the body. In such an embodiment, the base 31 comprises a first end 32, a second end 33, an outer surface 34, and an inner surface 35. The first end 32, the second end 33, or both ends 32, 33 of the base 31 may be removably or fixedly secured to the outer surface 23 of the strap 20. For example, in the embodiment shown in FIG. 3, the first end 32 of the base 31 is fixedly secured to the strap 20 while the second end 33 of the base 31 is removably secured to the strap 20 via a retainer connector 38, such as hook-and-loop fasteners. The base 31 preferably comprises a soft, cloth-like material to decrease discomfort to the individual 14 wearing it.

In the embodiment shown in FIGS. 10-13, the retainer connector 38 comprises a ring structure, with the strap 20 wrapping around the retainer connector 38 before the strap 20 connects to itself In the embodiment shown in FIG. 15, it is shown that the base 31 is optional; with the strap 20 being connected directly to the pouches 36, 37. In such an embodiment, the retainer connector 38 extends from the pouches 36, 37 and comprises a ring structure through which the strap 20 is extended before connecting to itself. It should be appreciated that various other types of retainer connectors 38 may be utilized so long as the strap 20 is secured to retainer attachment 30 at either a base 31 or the pouches 36, 37.

D. Pouches and Tube Retainers

Figure 19:
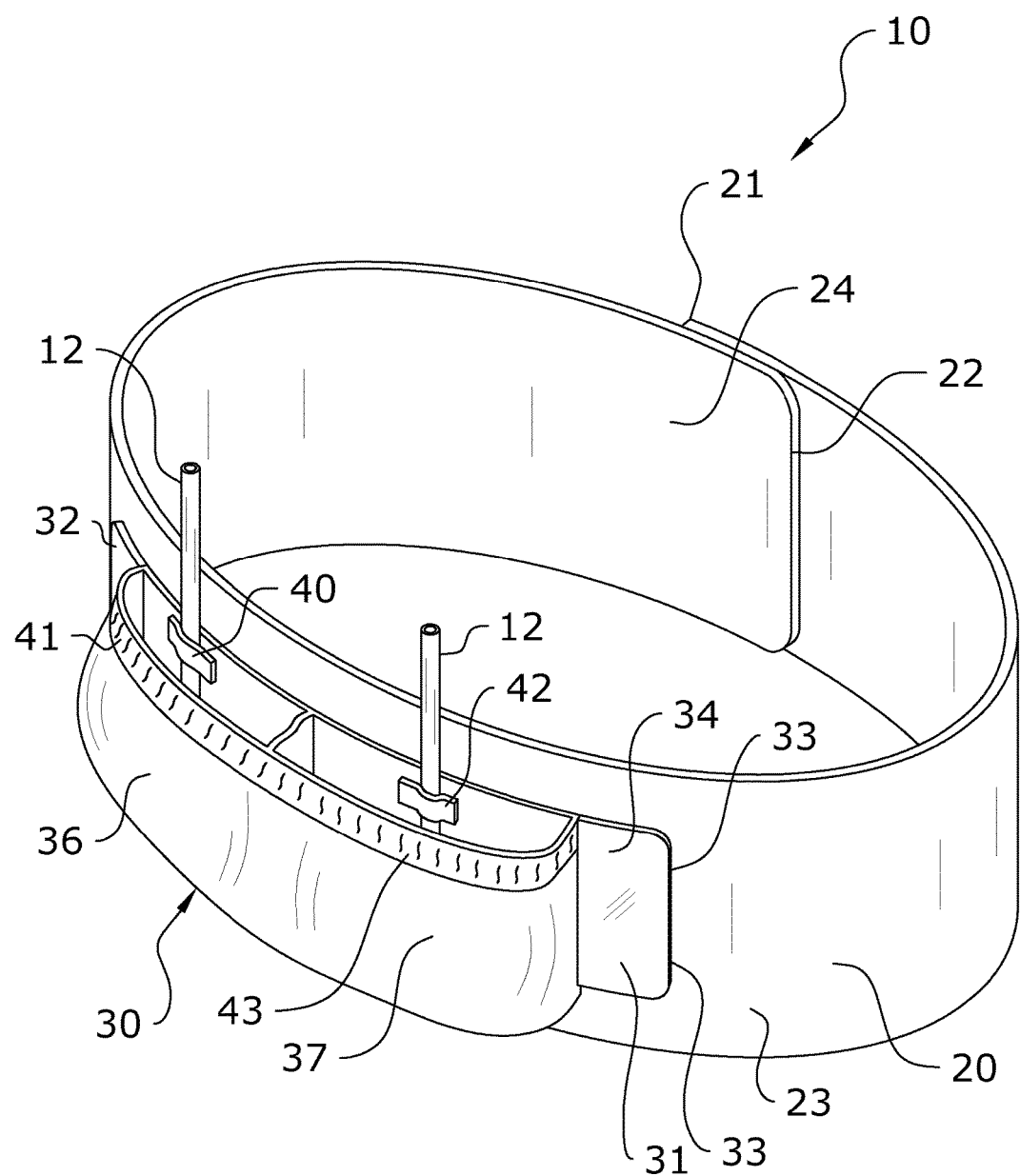
FIG. 19 is an upper perspective view of the present invention in which a cloth divider is utilized to separate the two pouches.

As shown throughout the figures, the retainer attachment 30 may include one or more pouches 36, 37 adapted to firmly and securely secure both the tube 12 and bulb 13 such that they do not move around or become compromised with movement of the individual 14. In the embodiment shown in the figures, a first pouch 36 and a second pouch 37 are utilized. However, it should be appreciated that more pouches 36, 37 may be utilized in some embodiments. The pouches 36, 37 may be divided by a sew-line as shown in FIGS. 1-11 (i.e. a singular pouch divided into two by sewing across a central area) or may be divided by a piece of cloth or other such divider as shown in FIG. 19. The use of a divider in the pouches 36, 37 is to distribute the contents, such that all the contents do not bunch up on one side.

Figure 16:
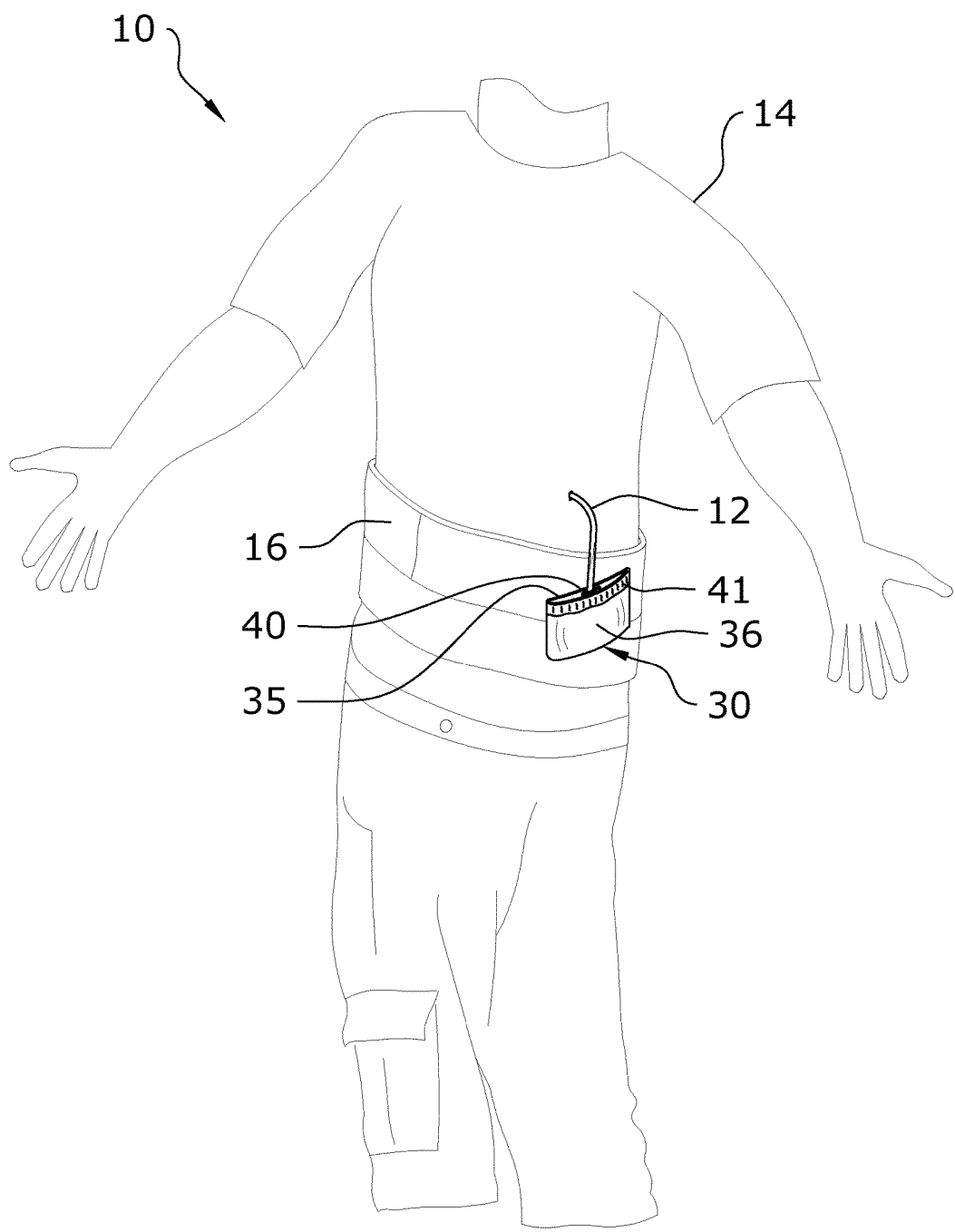
FIG. 16 is an upper perspective view of a pouch being retained on a bandage by a pouch retainer.
Figure 17:
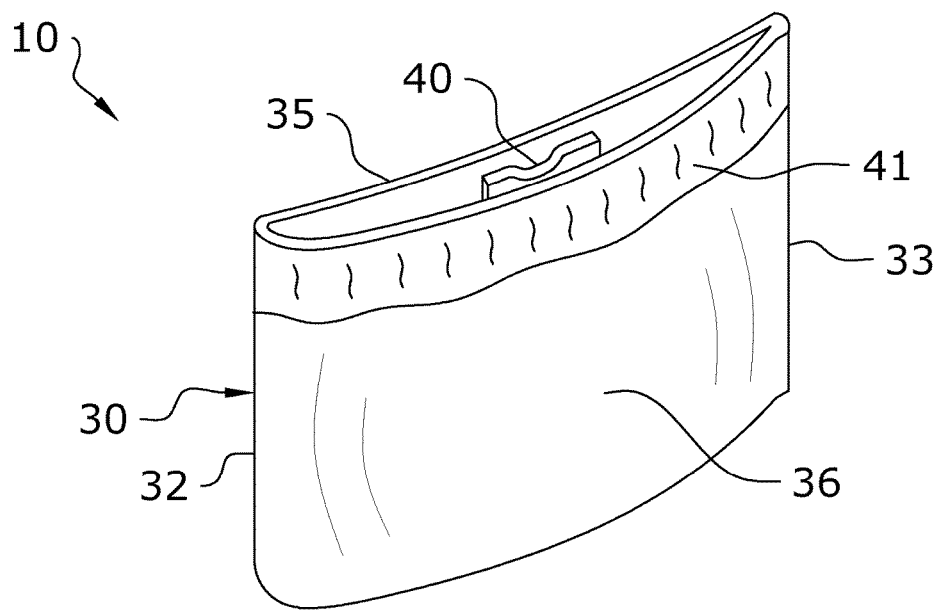
FIG. 17 is a frontal perspective view of a pouch of the present invention.
Figure 18:
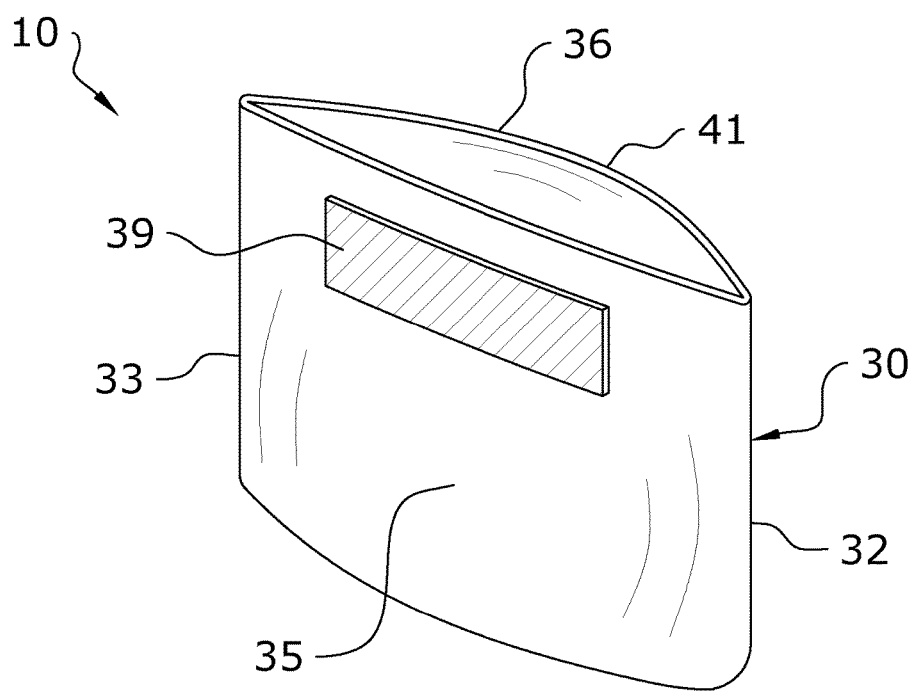
FIG. 18 is a rear perspective view of a pouch of the present invention.

The number, orientation, size, and configuration of the pouches 36, 37 should not be construed as limited by the exemplary figures. FIGS. 1-11, 14, 15, and 19 show a first pouch 36 and a second pouch 37. FIGS. 12-13 and 16-18 show a configuration which only utilizes a first pouch 36. Further, in the embodiment shown in FIGS. 16-18, it can be seen that a singular pouch may be provided having a pouch retainer 39 such as a hook-and-loop fastener. The pouch retainer 39 may be utilized to removably secure the pouch 36 to various other items, such as to some types of clothing, to a bandage 16 as shown in FIGS. 16-18, or to the base 31 of a retainer attachment 30.

The pouches 36, 37 may comprise various materials and should not be construed as being limited to any particular material. However, a mesh-like material is preferable for embodiments of the pouches 36, 37 that may be used in the shower or the like so that fluids do not pool up within the pouches. Embodiments not intended for use in a shower may omit the mesh-like material.

As shown in the figures, the pouches 36, 37 may include elastic 41, 43 at their respective upper ends. Thus, the first pouch 36 includes a first elastic 41 at its upper end and the second pouch 37 includes a second elastic 43 at its upper end. The elastics 41, 43 aid with opening the pouches 36, 37 up to place items inside or remove items therefrom. Absent force, the elastics 41, 43 will revert to their resting positions.

Each of the pouches 36, 37 includes tube retainers 40, 42 adapted to secure the tube 12 and bulb 13 within the respective pouch 36, 37. FIG. 2 illustrates an embodiment in which the first pouch 36 includes a first tube retainer 40 and the second pouch 37 includes a second tube retainer 42. The structure, positioning, orientation, and size of the tube retainers 40, 42 may vary in different embodiments of the present invention. The tube retainers 40, 42 may comprise straps which extend around the tube 12 before being secured via hook-and-loop fasteners or the like. The tube retainers 40, 42 may also comprise a flap of material, a clasp, a clip, or any other structure capable of securing the tube 12 within the pouch 36, 37.

In some embodiments, each pouch 36, 37 may include multiple tube retainers 40, 42 adapted to secure multiple tubes 12 and bulbs 13 within a single pouch 36, 37. Such an embodiment is shown in FIG. 7, in which the first pouch 36 includes a first retainer row 44 therein and the second pouch 37 includes a second retainer row 46 therein. In such an embodiment, the first retainer row 44 comprises a plurality of first tube retainers 40 and the second retainer row 46 comprises a plurality of second tube retainers 42.

E. Operation of Preferred Embodiment

In use, it is preferable that the strap 20 be secured around the body of an individual 14 before inserting the tubes 12 and bulbs 13. The strap 20 may be secured around various portions of the body, such as the shoulder, the waist, the stomach/mid-section, the leg, the arm, or the like. The strap 20 may be adjusted to ensure a secure fit around the body before attempting to secure the tubes 12 and bulbs 13.

Figure 6:
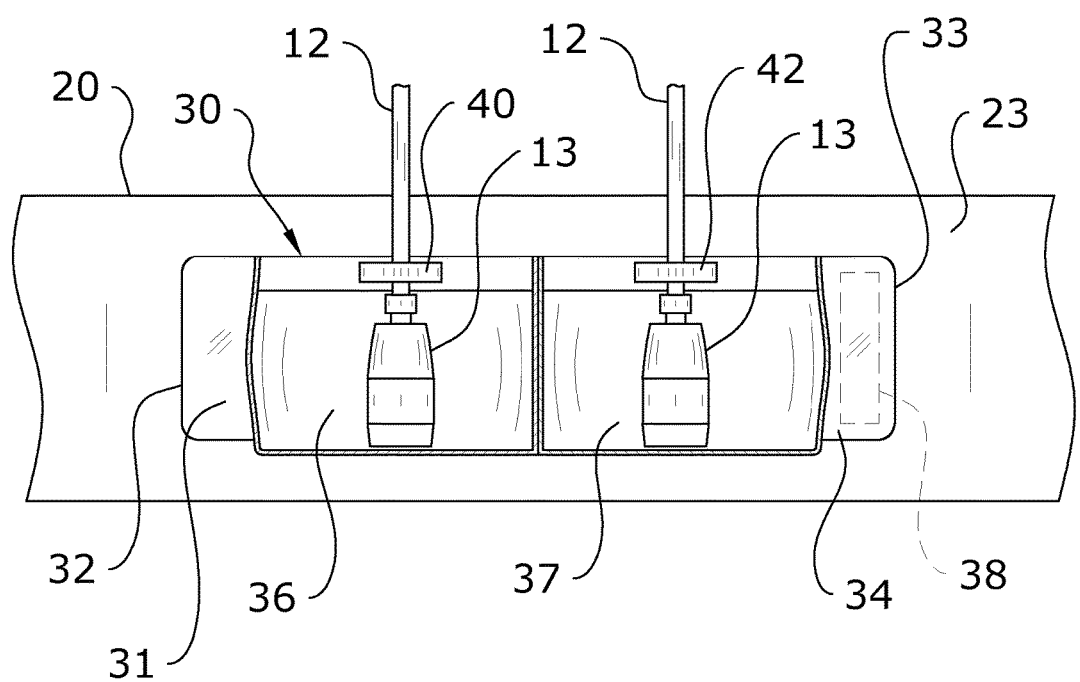
FIG. 6 is a frontal sectional view of the present invention.

With the strap 20 secured around the body at the desired area, the drainage tubes 13 may be routed from their entrance/exit of the body to the present invention. Each drainage tube 13 is secured within a tube retainer 40, 42 of the pouches 36, 37 of the retainer attachment 30. The bulb 13 itself, which acts as a reservoir for any fluids drained through the tube 13, may be secured within the pouch 36, 37 itself as shown in FIG. 6. The individual 14 may then proceed with their daily tasks secure with the knowledge that the tubes 12 and bulbs 13 are firmly secured within the present invention and thus are not likely to be moved around, disconnected, or otherwise compromised.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A drain tube holder system, comprising:
   a strap including a first end and a second end, wherein said first end of said strap is removably connected to said second end of said strap;
   a retainer attachment connected to said strap, wherein said retainer attachment includes a first pouch on an outer surface of the retainer attachment and defining an interior space sufficient to retain a reservoir bulb therein;
   the retainer attachment includes a first end and a second end, and:
     a) the first end includes a retainer connector that removably secures the first end to the strap, and the second end is fixedly secured to the strap; or
     b) each of the first end and the second end includes a respective retainer connector that removably secures the first end and the second end to the strap;
   the first pouch includes a first wall with an interior surface facing the interior space, a first side, a second side opposite the first side, a lower end, and an upper end opposite the lower end, the upper end being open to allow a drain tube that is connected to a reservoir bulb within the first pouch to extend therethrough; and
   the first pouch includes at least one tube retainer at the upper end thereof on the interior surface of the first wall, the at least one tube retainer is configured to secure a drain tube that extends through the upper end of the first pouch.

2. The drain tube holder system of claim 1, further comprising a second pouch next to the first pouch, the second pouch defining an interior space sufficient to retain a reservoir bulb therein, the first pouch and the second pouch are separated from one another by a divider with the divider forming part of the interior space of each of the first pouch and the second pouch;
   the second pouch includes a second wall with an interior surface facing the interior space thereof, a first side, a second side opposite the first side of the second pouch, a lower end, and an upper end opposite the lower end of the second pouch, the upper end of the second pouch being open to allow a drain tube that is connected to a reservoir bulb within the interior space of the second pouch to extend therethrough;
   the second pouch includes at least one tube retainer at the upper end thereof on the interior surface of the second wall, the at least one tube retainer of the second pouch is configured to secure a drain tube that extends through the upper end of the second pouch.

3. The drain tube holder system of claim 2, wherein said first pouch and said second pouch each comprise a mesh-like material.

4. The drain tube holder system of claim 2, further comprising first elastic at the upper end of the first pouch, and second elastic at the upper end of the second pouch.

5. The drain tube holder system of claim 1, wherein said strap is adapted to extend around a waist of an individual.

6. The drain tube holder system of claim 1, wherein said strap is adapted to extend around a shoulder of an individual.

7. The drain tube holder system of claim 1, further comprising a retainer connector for removably connecting said retainer attachment to said strap.

8. The drain tube holder system of claim 1, wherein said first end of said strap includes a first connector and wherein said second end of said strap includes a second connector.

9. The drain tube holder system of claim 8, wherein said first connector is adapted to removably attach to said second connector.

10. The drain tube holder system of claim 1, further comprising elastic at the upper end of the first pouch.

11. A drain tube holder system, comprising:
- a strap including a first end and a second end, wherein said first end of said strap is removably connected to said second end of said strap;
- a retainer attachment connected to said strap, wherein said retainer attachment includes a first pouch defining an interior space sufficient to retain a reservoir bulb therein;
- the first pouch includes a first side, a second side opposite the first side, a lower end, and an upper end opposite the lower end, the upper end being open to allow a drain tube that is connected to a reservoir bulb within the first pouch to extend therethrough; and
- the first pouch includes at least one tube retainer at the upper end thereof, the at least one tube retainer is configured to secure a drain tube that extends through the upper end of the first pouch;
- wherein said at least one tube retainer comprises a row of tube retainers at the upper end of the first pouch.

12. A drain tube holder system, comprising:
- a strap including a first end and a second end, wherein said first end of said strap is removably connected to said second end of said strap;
- a retainer attachment connected to said strap, wherein said retainer attachment includes a first pouch on an outer surface of the retainer attachment and defining an interior space sufficient to completely retain a reservoir bulb therein;
- the retainer attachment includes a first end and a second end, and:
  a) the first end includes a retainer connector that removably secures the first end to the strap, and the second end is fixedly secured to the strap; or
  b) each of the first end and the second end includes a respective retainer connector that removably secure the first end and the second end to the strap; and
- the first pouch includes a first side, a second side opposite the first side, a lower end, and an upper end opposite the lower end, the upper end being open to allow a drain tube that is connected to a reservoir bulb within the first pouch to extend therethrough.

* * * * *